United States Patent
Perouse

(10) Patent No.: US 7,927,363 B2
(45) Date of Patent: Apr. 19, 2011

(54) DEVICE FOR TREATING A BLOOD VESSEL AND ASSOCIATED TREATMENT KIT

(75) Inventor: Eric Perouse, Paris (FR)

(73) Assignee: Laboratoires Perouse, Ivry Le Temple (FR)

( * ) Notice: Subject to any disclaimer, the term of this patent is extended or adjusted under 35 U.S.C. 154(b) by 231 days.

(21) Appl. No.: 11/605,352

(22) Filed: Nov. 29, 2006

(65) Prior Publication Data

US 2007/0100427 A1 May 3, 2007

(30) Foreign Application Priority Data

Dec. 2, 2005 (FR) ..................... 05 12265

(51) Int. Cl.
*A61F 2/06* (2006.01)
(52) U.S. Cl. ............... 623/1.12; 623/1.11; 623/1.17
(58) Field of Classification Search .............. 623/1, 1.1, 623/11.11, 11.12, 11.15, 11.16, 11.17; 604/43
See application file for complete search history.

(56) References Cited

U.S. PATENT DOCUMENTS

| 5,554,183 | A | * | 9/1996 | Nazari ................... 623/1.49 |
| 5,743,918 | A | * | 4/1998 | Calandruccio et al. ....... 128/898 |
| 6,302,891 | B1 | | 10/2001 | Nadal |
| RE38,091 | E | | 4/2003 | Strecker |
| 2002/0038144 | A1 | | 3/2002 | Trout, III et al. |
| 2003/0225445 | A1 | * | 12/2003 | Derus et al. ................. 623/1.11 |

FOREIGN PATENT DOCUMENTS

EP 0 664 107 7/1995
WO 97/48350 12/1997

* cited by examiner

*Primary Examiner* — David Isabella
*Assistant Examiner* — Joshua Levine
(74) *Attorney, Agent, or Firm* — Wenderoth, Lind & Ponack, L.L.P.

(57) ABSTRACT

A tubular endoprosthesis can be radially deployed between a retracted state and an expanded state. It includes an axially rigid support which has at least one retention opening. The device further includes at least one filamentary connection which has a region for clamping the endoprosthesis, at least partially surrounding the endoprosthesis, and a control region which is connected to the clamping region via the retention opening. The support is permanently fixed to the endoprosthesis.

17 Claims, 4 Drawing Sheets

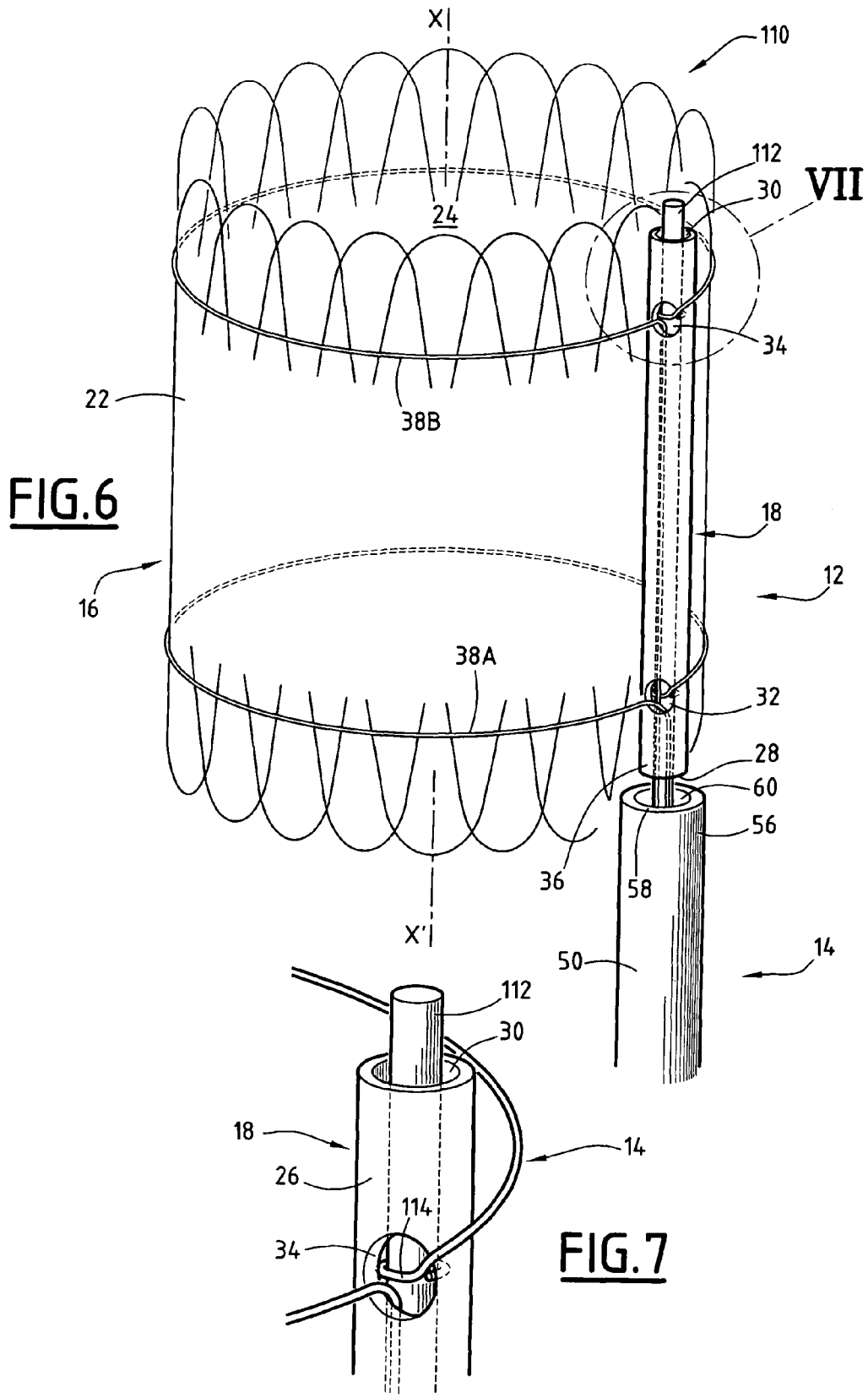

DEVICE FOR TREATING A BLOOD VESSEL AND ASSOCIATED TREATMENT KIT

TECHNICAL FIELD

The present invention relates to a device for treating a blood circulation canal, of the type including a tubular endoprosthesis which can be radially deployed between a retracted state and an expanded state; an axially rigid support which has at least one retention opening; and at least one filamentary connection. The connection comprises a region for clamping the endoprosthesis, at least partially surrounding the endoprosthesis, and a control region which is connected to the clamping region via the retention opening.

A device of this type is used in particular for releasing, in a blood vessel, tubular endoprostheses, commonly referred to as "stents", or tubular endovalves which comprise a tubular endoprosthesis and a valve which is fixed to the endoprosthesis.

BACKGROUND TO THE INVENTION

A device of the above-mentioned type is described in EP-A-0 707 462. An endoprosthesis is mounted coaxially on two hollow tubes which are capable of sliding relative to each other. This endoprosthesis is retained in the retracted state thereof by two filamentary connections which surround it at the ends thereof. The filamentary connections are engaged in distal and proximal retention openings which are arranged in one support and the other, respectively.

In order to release the endoprosthesis, the supports are displaced by relative sliding in a first direction in order to release the filamentary connections and simultaneously deploy the two ends of the endoprosthesis. If the positioning of the endoprosthesis is not satisfactory, the filamentary connections can be tightened by sliding the supports in the opposite direction, which brings about the contraction of the endoprosthesis.

When the positioning of the endoprosthesis is satisfactory, the filamentary connections are removed.

A device of this type is not entirely satisfactory. This system has a complex structure which may compromise the reliability of the release operation.

SUMMARY OF THE INVENTION

The object of the invention is to provide a device for treating a blood vessel which can be released in a reversible manner in a blood vessel, without the reliability thereof being reduced.

To this end, the invention relates to a treatment device of the above-mentioned type, wherein the support is permanently fixed to the endoprosthesis.

The device according to the invention may comprise one or more of the following features, taken in isolation or according to any technically possible combination. The endoprosthesis can have a peripheral wall, the support being fixed at least at two points which are axially spaced from the peripheral wall. The peripheral wall can delimit internally a channel for passage of a fluid, the support being fixed to the peripheral wall at the outer side of the passage channel. The support can extend axially substantially over the entire length of the endoprosthesis. The support can delimit internally an aperture which opens in the or each passage opening and in at least one control opening which is spaced longitudinally from the or each passage opening. The or each filamentary connection can have a gripping end which protrudes from the support through the control opening, the gripping end forming a traction loop. The control region can include two strands which are connected to the traction loop and to two separate points of the clamping region. The endoprosthesis can include at least two filamentary connections which comprise two clamping regions which are axially spaced on the endoprosthesis. The gripping ends of the two connections from a traction loop common to the two connections. The endoprosthesis can include at least two filamentary connections, the support delimiting a proximal control opening and a distal control opening. The gripping ends of the two connections protrude through the proximal control opening and the distal control opening, respectively. The traction loop can include a ring which is fixedly joined to the control region, the ring having a transverse extent which is greater than that of the control opening. At least one filamentary connection can be releasable.

The invention further relates to a treatment kit, of the type including a device as defined above. In addition, the kit includes a means for releasing and/or recovering the device. The means includes a rigid rod which has a distal support surface for the device; and a means for traction of the or each filamentary connection which are capable of gripping the or each control region.

The treatment kit may also include the following features. The or each filamentary connection can have a gripping end which forms a traction loop. The traction means can include, for engaging the gripping end, an elongated hook member which is mounted so as to be able to be moved in the rigid rod between a deployed position for engagement of the gripping end and a retracted position for traction of the gripping end.

BRIEF DESCRIPTION OF THE DRAWINGS

The invention will be better understood from a reading of the following description, given purely by way of example, and with reference to the appended drawings, in which:

FIG. 6 is a view similar to FIG. 1, drawn to an enlarged scale, of a third kit according to the invention;

FIG. 7 is a view of a detail designated VII in FIG. 6.

DETAILED DESCRIPTION OF THE PREFERRED EMBODIMENTS

FIGS. 1 to 4 illustrate a first kit 10 according to the invention, comprising a treatment device 12 which is intended to be released in a blood circulation canal, and a positioning member 14 for releasing and recovering the device 12.

Figure 1:
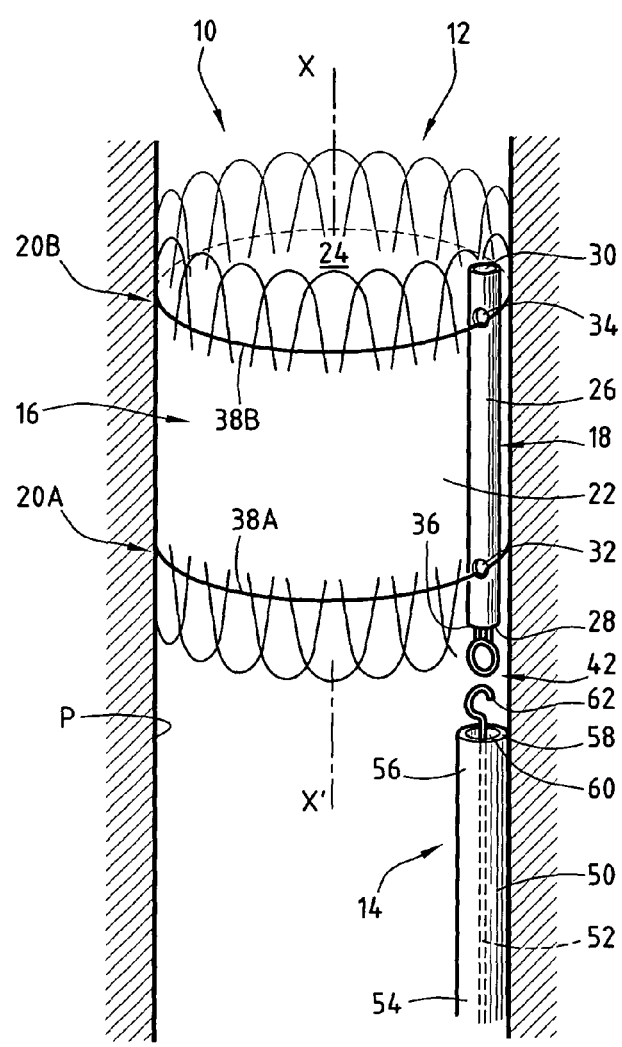
FIG. 1 is a partial perspective view of a first treatment kit according to the invention, including an endoprosthesis which is deployed in a blood vessel.

As illustrated in FIG. 1, the device 12 comprises a tubular endoprosthesis 16 having an axis X-X', an axially rigid support 18 which is permanently fixed to the endoprosthesis 16, and two filamentary connections 20A, 20B which at least partially surround the endoprosthesis 16 in the region of the proximal and distal ends thereof.

The endoprosthesis 16 comprises in a known manner a tubular trellis of stainless steel which has spring-like properties.

This endoprosthesis is, for example, produced by braiding a single thread of a super-resilient material as described in the European patent application EP-A-0 857 471.

The tubular trellis delimits, at the ends of the endoprosthesis 16, a plurality of interlocking elbow-like joints.

The tubular trellis forms a peripheral wall 22 which internally delimits a channel 24 having an axis X-X'. The trellis is, for example, embedded in a flexible elastomer film in order to produce a sealed wall around the channel 24.

Figure 2:
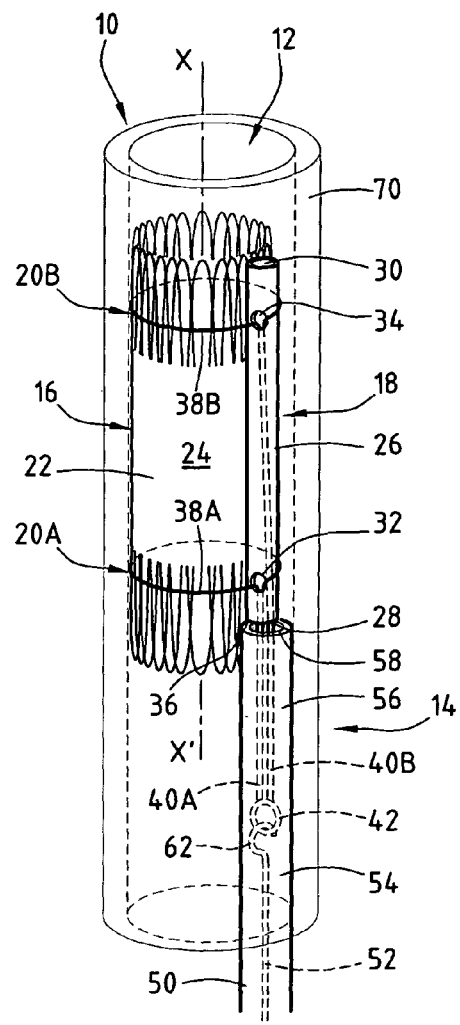
FIG. 2 is a view similar to FIG. 1, before the endoprosthesis is released in the blood vessel.

As known per se, the endoprosthesis 16 is capable of deforming spontaneously from a retracted state illustrated in FIG. 2, in which it has a small diameter, into an expanded state illustrated in FIG. 1, in which it has a larger diameter. This expanded state constitutes the rest state thereof.

The support 18 comprises a hollow post member 26 which extends axially and which is fixed in at least two points which are axially spaced at the outer side of the peripheral wall 22.

In the example illustrated, the post member 26 is fixed continuously to the peripheral wall 22 along a directrix of the peripheral wall 22.

Figure 3:
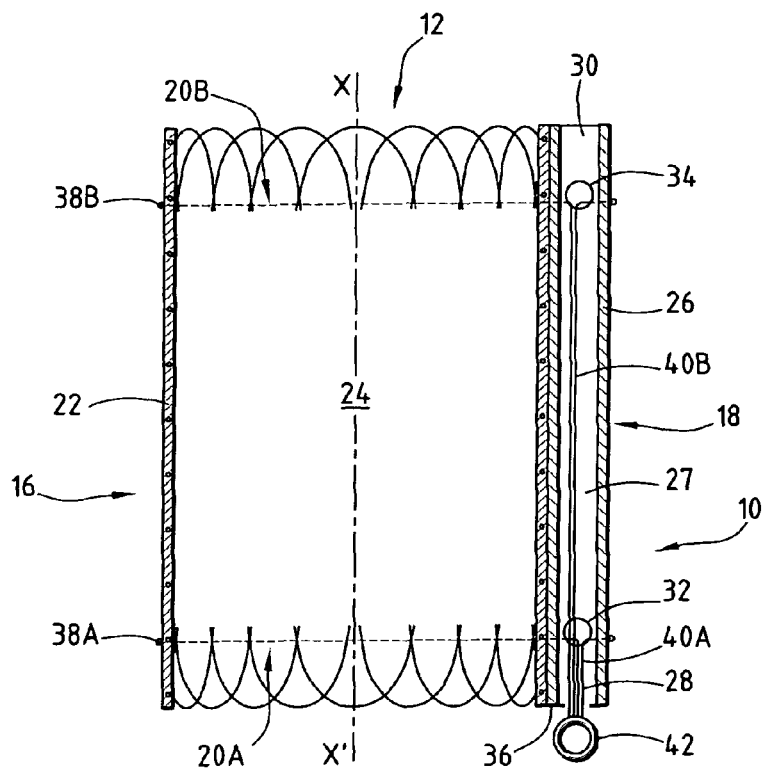
FIG. 3 is a sectioned view along a central axial plane of the relevant portions of the kit of FIG. 1.
Figure 4:
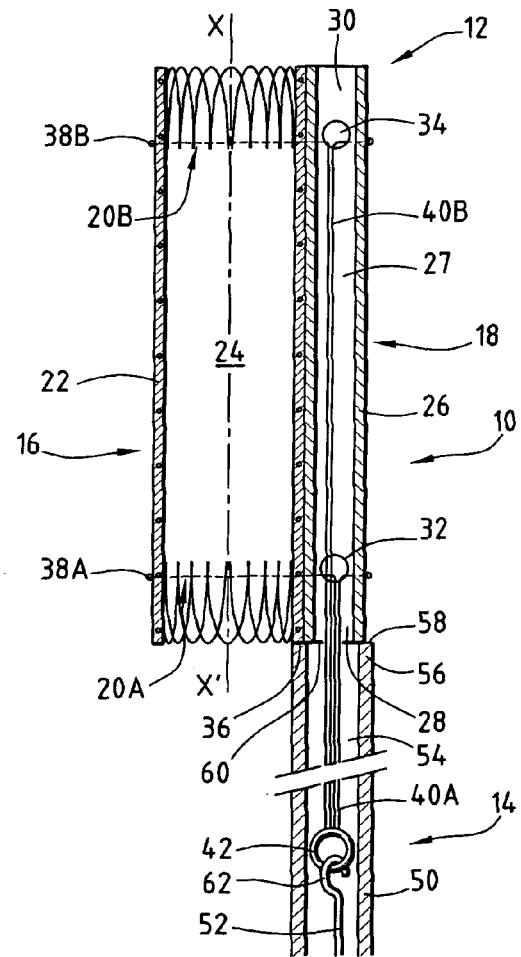
FIG. 4 is a view similar to FIG. 3 of the kit in the configuration illustrated in FIG. 2.

As illustrated in FIG. 3, the post member 26 internally delimits a central aperture 27 which extends axially and which opens at the ends thereof via a proximal axial control opening 28 and a distal axial control opening 30.

The post member 26 delimits, in the region of the proximal opening 28 and the distal opening 30, respectively, a transverse proximal retention opening 32 and a transverse distal retention opening 34, through which the proximal connection 20A and the distal connection 20B are engaged, respectively.

The support 18 further delimits, around the proximal control opening 28, an annular surface 36 for supporting the positioning member 14.

Each retention thread 20A, 20B comprises a clamping region 38A, 38B which forms a loop which surrounds the endoprosthesis in the region of one of the ends thereof, and at least one control region 40A, 40B which is arranged in the support 18 and which has a proximal gripping end which protrudes through the proximal control opening 28 and beyond the proximal end of the endoprosthesis even in the expanded state of the endoprothesis, as shown in FIGS. 1 and 3. The gripping ends are fixed to a traction loop 42 which is common to the connections 20A, 20D.

The clamping region 38A, 38B is formed by a single strand of thread arranged around a circumference of the endoprosthesis 16.

In a variant, the clamping region may be engaged in the trellis of the endoprosthesis 16, moving successively inside and outside the trellis.

Each control region 40A, 40B is formed by two strands of thread which are connected to two ends of an associated clamping region 38A, 38B, respectively, via a corresponding retention opening 32, 34. The strands extend substantially axially in the passage 27 as far as the traction loop 42 to which they are fixed.

The traction loop 42 comprises a ring which has a transverse extent (outer diameter) greater than the transverse extent (inner diameter) of the proximal control opening 28. The ring is produced from a radio-opaque material.

A traction of the ring 42 in a proximal direction allows the length of the control regions 40A, 40B of the connections 20A, 20B to be simultaneously increased, whilst reducing the length of the clamping regions 38A, 38B which thus brings about the contraction of the endoprosthesis 16 as will be described below.

The positioning member 14 for releasing and recovering the endoprosthesis 16 includes a rigid hollow rod 50 and, for catching of the loop 42, an elongated hook member 52 which is mounted so as to be able to move along the rod 50 in a central passage 54 which is provided in the rod 50.

The rigid rod 50 extends between a proximal end (not illustrated) which is intended to be accessible to a surgeon, and a distal end 56 which is intended to be placed in the blood canal to be treated.

The distal end 56 has an annular support surface 58 for the support 18, delimiting an opening 60 for passage of the elongate hook member 52 in which the central passage 54 opens.

The elongate hook member 52 has a head 62 in the form of a hook. The elongate hook member 52 can be moved between a deployed position in which the head 62 protrudes from the distal end 56 and a retracted position for retracting of the loop 42 in which the head 62 is arranged inside the central passage 54.

In order to release the device 12 in a vessel, the positioning member 14 further comprises an outer sheath 70 which internally receives the device 12 in the retracted state thereof and the rigid rod 50 provided with the elongate hook member 52.

The operation of the first treatment kit 10 according to the invention will now be described. Initially, the kit 10 is stored in a sterile packaging. In this packaging, the endoprosthesis 16 is maintained in the rest state in the expanded state thereof. The clamping regions 38A, 38B of the connections 20A, 20B of the endoprosthesis have a maximum length and the control regions 40A, 40B have a minimal length. The traction loop 42 is positioned in the vicinity of the proximal control opening 28 whilst being retained with spacing from this opening 28 in order to retain the filamentary connections 20A, 20B in a slack state.

When the surgeon wishes to place the endoprosthesis 16 in the sheath 70, he inserts the hook 62 at the end of the elongated hook member 52 in the traction loop 42. Then, he moves the support surface 58 of the rigid rod 50 towards the annular support surface 36 of the post member 26.

Then, when the support surfaces 36 and 58 are in contact, he moves the elongate hook member 52 towards the retracted position thereof which pulls the traction loop 42 towards the proximal end of the rigid rod 50.

Since the annular surface 36 is arranged so as to be supported on the annular surface 58, the post member 26 and the endoprosthesis 16 which is fixedly joined (permanently fixed) to the post member remain axially fixed to the distal end 56 of the rigid rod 50.

The proximal displacement of the traction loop 42 brings about an increase of the length of the control regions 40A, 40B of the connections 20A, 20B and a corresponding reduction of the length of the clamping regions 38A, 38B.

The endoprosthesis 16 is thus brought into the retracted state thereof by the filamentary connections 20A, 20B. The assembly formed by the treatment device 12 and the rigid rod 50 provided with the elongated hook member 52 is then inserted into the sheath 70.

Then, the sheath 70 is introduced into the patient as far as the blood circulation canal in which the device 12 must be deployed.

The surgeon then removes the device 12 from the sheath 70 by moving the sheath 70 in a proximal direction, whilst keeping the treatment device 12 axially fixed using the rigid rod 50, by means of co-operation between the support surfaces 58 and 36. The position of the endoprosthesis in the blood vessel is therefore very precise, even if the blood circulates with a counter current in the vessel.

The elongated hook member 52 is then moved towards the distal end 56 of the rod 50. Under the action of the resilience of the trellis which constitutes the endoprosthesis 16, the endoprosthesis deploys from the retracted state to the expanded state thereof until the peripheral wall 22 of the endoprosthesis 16 comes into contact with the wall P of the vessel to be treated.

During this movement, the traction loop 42 moves closer to the proximal control opening 28 so that the length of the control regions 40A, 40B decreases and the length of the clamping regions 38A, 38B increases.

If the surgeon considers that the positioning of the device 12 is unsatisfactory, he can pull on the elongate hook member 52 in order to move the hook 62 towards the proximal end of the rod 50 and again bring about the contraction of the endoprosthesis 16. The surgeon then replaces the endoprosthesis in a more satisfactory manner in the canal as described above.

When he considers that the position of the endoprosthesis 16 is satisfactory, the surgeon removes the hook 62 from the traction loop 42 and extracts the rigid rod 50 and the elongated hook member 52 from the patient.

If the endoprosthesis 16 subsequently has to be removed, the rigid rod 50 is again introduced into the blood vessel. Then, the hook 62 of the elongate hook member 52 can be engaged in the traction loop 42 in order to retract the endoprosthesis 16 as described above.

Since the traction loop 42 is produced using a ring of radio-opaque material, gripping of the ring using the elongated hook member 52 is facilitated.

Figure 5:
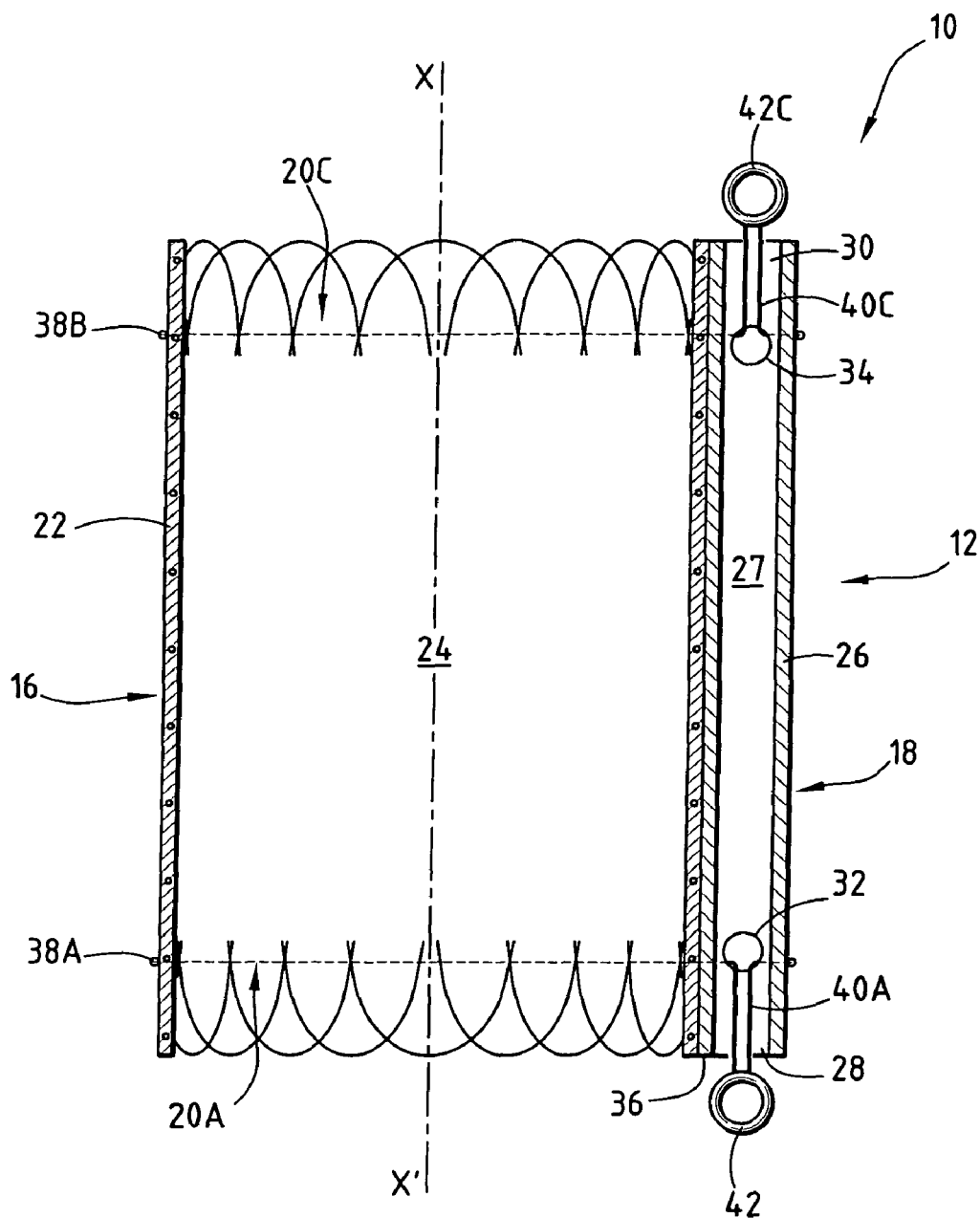
FIG. 5 is a view similar to FIG. 3 of a second kit according to the invention.

In a first variant which is partially illustrated in FIG. 5, the device 12 comprises at least one filamentary connection 20C which comprises a clamping region 38C which surrounds the endoprosthesis and a control region 40C whose end protrudes through the distal control opening 30. This end is further provided with a loop 42C which is arranged in the vicinity of the proximal end when the endoprosthesis 16 is in the expanded state thereof.

This device 12 allows the at least partial contraction of the endoprosthesis 16 using a rod 50 which is introduced via a portion of the blood vessel that is distal relative to the device 12.

The treatment device 110 illustrated in FIGS. 6 and 7 differs from the device 10 illustrated in FIGS. 1 to 4 in that the filamentary connections 20A, 20B can be released.

To this end, the elongated hook member 52 is replaced with a retention pin 112 which is engaged in the rod 50 and in the central passage 54 of the post member 26.

The clamping region 38A, 38B comprises, at one end, a loop 114 which is engaged round the pin 112 in the passage 27, via a retention opening 32, 34.

The control region 40A, 40B comprises a single strand which extends longitudinally as far as the proximal end of the rigid rod 50.

Initially, in order to retract the endoprosthesis 16, the surgeon pulls on the proximal end of each control region 40A, 40B at the proximal end of the rigid rod 50.

Since the clamping regions 38A, 38B of each connection 20A, 20B are retained by the loop 114 which is engaged on the pin 112, the length of each clamping region 38A, 38B decreases, which brings about the contraction of the endoprosthesis 16.

Then, when the device 10 is introduced into the vessel to be treated, each control region 40A, 40B is relaxed which brings about an increase in the length of the clamping region 38A, 38B under the action of the radial expansion of the endoprosthesis 16.

When the endoprosthesis 16 is placed in a satisfactory manner in the vessel to be treated, the pin 112 is removed from the post member 26, and is then extracted from the patient via the rigid rod 50.

The loops 114 are thus released. The surgeon can then pull on the proximal end of each connection 20A, 20B in order to remove them from the patient.

Using the invention which has been described above, it is possible to provide a treatment device 12 which comprises an endoprosthesis 16 which can be deployed and which can be implanted in a reversible manner in a blood vessel.

The presence of a support 18 which is permanently fixed to the endoprosthesis and which receives at least one connection 20A, 20B for clamping the endoprosthesis 16 ensures the precise positioning of the endoprosthesis 16 when it is deployed, whilst simplifying the device required for the release thereof in the vessel.

Furthermore, when a connection 20A, 20B is permanently retained on the endoprosthesis 16, it is possible to remove the endoprosthesis 16 from the vessel via an endoluminal route when it has to be replaced.

The invention claimed is:

1. A treatment device for treating a blood circulation canal, comprising:
   a tubular endoprosthesis operable to be radially deployed between a retracted state and an expanded state;
   an axially rigid support which has a retention opening, said support extending axially substantially over an entire length of said endoprosthesis; and
   a filamentary connection having a clamping region for clamping said endoprosthesis, said clamping region at least partially surrounding said endoprosthesis, and a control region connected to said clamping region via said retention opening of said support, said control region having a proximal gripping end protruding beyond a proximal end of said endoprosthesis when said endoprosthesis is in the expanded state;
   wherein said rigid support is permanently fixed to said endoprosthesis.

2. The treatment device of claim 1, wherein said endoprosthesis comprises a peripheral wall, said support being fixed to said peripheral wall at least at two points at an outer surface of said peripheral wall, said at least two points being axially spaced apart.

3. The treatment device of claim 2, wherein an entire length of said support is fixed continuously along said peripheral wall of said endoprosthesis, along an axial direction of said peripheral wall.

4. The treatment device of claim 2, wherein said peripheral wall delimits an internal channel in said endoprosthesis for allowing passage of a fluid, said support being fixed to said peripheral wall at an outer side of said passage channel.

5. The treatment device of claim 1, wherein said support has an internal aperture which communicates with a passage opening and a control opening, said control opening being longitudinally spaced from said passage opening.

6. The treatment device of claim 5, wherein said proximal gripping end protrudes from said support through said control opening, said proximal gripping end having a traction loop.

7. The treatment device of claim 6, wherein said control region of said filamentary connection comprises two strands connected to said traction loop, and connected to two separate points of said clamping region.

8. The treatment device of claim 6, wherein said filamentary connection comprises a first filamentary connection, further comprising a second filamentary connection, said first filamentary connection and said second filamentary connection each having a gripping end and comprising two clamping regions axially spaced apart on said endoprosthesis, said gripping ends of said first filamentary connection and said second filamentary connection sharing a common traction loop and forming said proximal gripping end of said control region.

9. The treatment device of claim 6, wherein said filamentary connection comprises a first filamentary connection, further comprising a second filamentary connection having a gripping end, said support having an internal central aperture extending axially and having a proximal axial control opening and a distal axial control opening at ends of said support, said gripping end of said first filamentary connection protruding through said proximal axial control opening, and said gripping end of said second filamentary connection protruding through said distal control opening, said gripping end of said first filamentary connection and said gripping end of said second filamentary connection forming said proximal gripping end of said control region.

10. The treatment device of claim 6, wherein said traction loop comprises a ring fixed to said control region, said ring having an outer diameter greater than an inner diameter of said control opening.

11. The treatment device of claim 1, wherein said endoprosthesis is operable to spontaneously expand when said clamping region of said filamentary connection releases said endoprosthesis.

12. A treatment kit comprising:
a treatment device as recited in claim 1; and
a positioning member for releasing and recovering said device, said positioning member including:
a rigid rod having a distal support surface for engaging and supporting said device; and
a traction member operable to grip said control region of said filamentary connection.

13. The kit of claim 12, wherein an entire length of said support is fixed continuously along said peripheral wall of said endoprosthesis, along an axial direction of said peripheral wall.

14. The kit of claim 13, wherein said proximal gripping end protrudes from said support through a control opening, said proximal gripping end having a traction loop.

15. The kit of claim 14, wherein said control region of said filamentary connection comprises two strands connected to said traction loop, and connected to two separate points of said clamping region.

16. The kit of claim 12, wherein said proximal gripping end has a traction loop, said traction member comprising an elongated hook member for engaging said proximal gripping end of said filamentary connection, said elongated hook member being mounted so as to be movable within said rigid rod between a deployed position for engagement of said proximal gripping end and a retracted position for traction of said gripping end.

17. A method of positioning the treatment device of claim 1, comprising:
providing an implantation and recovery device including a rigid rod having a distal support surface for engaging and supporting the treatment device, and a traction member operable to grip the control region of the filamentary connection;
engaging the traction member with the proximal gripping end of the control region protruding beyond the proximal end of the endoprosthesis while the endoprosthesis is in the expanded state;
contacting the distal support surface of the rigid rod with a support surface of the support;
moving the traction member towards a retraction position in a direction towards a proximal end of the rigid rod so as to thereby pull a traction loop at the proximal gripping end of the control region towards the proximal end of the rigid rod to thereby radially retract the endoprosthesis into the retracted state; and
positioning the endoprosthesis after the endoprosthesis is retracted into the retracted state, said positioning comprising one of implanting the endoprosthesis within a blood circulation canal or recovering the endoprosthesis from the blood circulation canal.

* * * * *